(12) United States Patent
Raffer

(10) Patent No.: US 9,255,872 B2
(45) Date of Patent: Feb. 9, 2016

(54) PROCESS FOR DETERMINING THE RHEOLOGICAL PROPERTIES OF MATERIALS

(71) Applicant: ANTON PAAR GMBH, Graz-Strassgang (AT)

(72) Inventor: Gerhard Raffer, Graz (AT)

(73) Assignee: Anton-Paar GmbH, Graz-Strassgang (AT)

(*) Notice: Subject to any disclaimer, the term of this patent is extended or adjusted under 35 U.S.C. 154(b) by 356 days.

(21) Appl. No.: 13/932,172

(22) Filed: Jul. 1, 2013

(65) Prior Publication Data

US 2013/0298645 A1   Nov. 14, 2013

Related U.S. Application Data

(62) Division of application No. 12/768,248, filed on Apr. 27, 2010, now Pat. No. 8,499,619.

(30) Foreign Application Priority Data

Apr. 28, 2009   (AT) .................................. A 648/2009

(51) Int. Cl.
    *G01N 11/14*   (2006.01)
(52) U.S. Cl.
    CPC .............. *G01N 11/14* (2013.01); *G01N 11/142* (2013.01)
(58) Field of Classification Search
    CPC ............................ G01N 11/14; G01N 11/142
    USPC .................... 73/54.28, 54.37, 54.38, 54.39
    See application file for complete search history.

(56) References Cited

U.S. PATENT DOCUMENTS

| 6,167,752 B1 | 1/2001 | Raffer |
| 6,499,336 B1 | 12/2002 | Raffer |
| 7,181,956 B2 | 2/2007 | Platzek et al. |
| 2012/0240665 A1 | 9/2012 | Wilkinson et al. |

FOREIGN PATENT DOCUMENTS

| AT | 404192 | 9/1998 |
| AT | 409304 | 7/2002 |
| DE | 19632589 A1 | 2/1998 |
| DE | 102004050753 A1 | 4/2006 |
| EP | 0043892 A1 | 1/1982 |
| GB | 2356937 A | 6/2001 |
| SU | 613227 A1 | 6/1978 |
| WO | 2010013066 A1 | 2/2010 |

*Primary Examiner* — Daniel S Larkin
(74) *Attorney, Agent, or Firm* — Laurence A. Greenberg; Werner H. Stemer; Ralph E. Locher

(57) ABSTRACT

A process and an apparatus determine the rheological properties of medium samples. The normal forces arising in a measuring gap perpendicular to the measuring surfaces are recorded with a recording unit and the height of the measuring gap is adjusted with a positioning unit and with positioning elements actuated by the positioning unit. During the measuring procedure the initial height of the measuring gap is kept constant, by the values of the normal forces arising being linked with a calibrating function, and in that, upon detection of normal forces arising, values derived from the calibrating function are drawn upon as control signals, with which at least one sliding actuator acting on at least one of the two measuring elements is driven, which by position adjustment or height adjustment of the respective measuring element performs an immediate resetting of a height of the measuring gap, changed by the normal forces exerted by the medium sample to be examined, to the initial spacing set originally.

4 Claims, 7 Drawing Sheets

PROCESS FOR DETERMINING THE RHEOLOGICAL PROPERTIES OF MATERIALS

CROSS-REFERENCE TO RELATED APPLICATION

This is a divisional of patent application No. 12/768,248, filed Apr. 27, 2010 now U.S. Pat. No. 8,499,619; the application also claims the priority, under 35 U.S.C. §119, of Austrian Patent Application No. A 648/2009, filed Apr. 28, 2010; the prior applications are herewith incorporated by reference in their entirety.

BACKGROUND OF THE INVENTION

Field of the Invention

The invention relates to a process for determining the rheological properties of samples of a medium, in particular of viscous and viscoelastic substances, which are arranged in a measuring gap formed by measuring surfaces facing towards one another of two measuring elements of a rotary rheometer which are rotated relative to one another. The normal forces arising in the measuring gap perpendicular to the measuring surfaces are recorded with a recording unit and are evaluated in an evaluating and control unit. A height of the measuring gap is adjusted with a positioning unit and with positioning elements actuated by the positioning unit. The positioning unit adjusts the positioning elements carrying the respective measuring element. The invention further relates to a rheometer.

In rotary rheometers of such a type, two measuring elements of defined geometry, at least one of which is driven in rotation, for example cup-type measuring bodies, plate-plate or plate-cone, are mounted, at an adjustable, constant axial or constantly maintained spacing from one another, on a stand or rack, and the medium sample to be examined or gauged in respect of its rheological properties is introduced into the measuring gap formed between these two measuring elements. As a result of the influence of the properties of the medium sample during the measurement, changes occur in the height of the gap between the measuring elements, or a deceleration of the measuring element being rotated occurs.

An instrument of such a type is described in U.S. Pat. No. 6,167,752 and its counterpart Austrian Patent AT 404 192 B, for example. In this instrument two measuring elements of defined geometry—specifically, for example, cups with measuring body, plate-plate or plate-cone —are guided on a stand in vertically adjustable manner at, in each case, a settable, constant axial spacing from one another by positioning elements, and the sample to be gauged is introduced into the measuring gap formed between these two measuring elements. The two measuring elements are set in rotary motion relative to one another by a motor-driven drive shaft, and as a result a shearing string and/or transverse string is exerted on the sample medium. The resistance opposed to this rotation/shearing by the sample medium is expressed in a torque acting on the measuring elements and is a measure of the rheological properties of the substance being examined.

For the test procedure, differently shaped measuring elements can be fitted to positioning elements of the rheometer. The measuring elements are brought to the desired spacing relative to one another before or after the sample medium is introduced, in which connection the zero point of the gap is, where appropriate, measured previously for the purpose of relative determination of the height of the gap.

Depending on the type of instrument, in this connection the upper measuring element rotates, for example in accordance with Searle's method, or the lower measuring element, for instance a measuring cup, rotates, for example in accordance with Couette's method. The resulting torque and/or the phase position is/are determined.

The determination of the torque can be undertaken by a motor configured for drive and for torque measurement, or alternatively via two units, separated from one another, for determination of rotation and torque, which are each assigned to one of the measuring elements.

In FIG. 1 a known embodiment of a rotary rheometer 100 is represented. A medium sample 19 which to be gauged is located in a gap 1 which is formed between the two plate-shaped measuring elements 1a, 1b. A measuring motor 2 drives in rotation a measuring shaft 3 and the upper measuring element 1a is connected to the shaft. In this connection the relationship between the torque on the measuring shaft 3 and the power consumption of the measuring motor 2 is known exactly or can be ascertained by calibration. An angle encoder 4 enables the determination of angle of rotation and speed of rotation. All the values are available in an evaluating unit 13. Normal forces arising are measured with the measuring unit 6.

The rheological characteristic values of the medium sample 19 are ascertained in the evaluating unit 13 from the torque or from the supply parameters, in particular from the power consumption of the measuring motor 2 and/or from the frequency and/or the phase position of the measuring shaft 3 and the gap data, taking measuring-geometry data and the temperature into account.

Alternatively, constant rotational speeds and hence the rates of shear can be preset for the test procedure (CSR test—controlled shear rate test), and the torque is measured, or alternatively the torque or the shearing stress is preset and held constant (CSS test—controlled shear stress test), and the change in the rotational speed is measured.

As a further type of test, oscillation tests are also available. In this case the measuring shaft has oscillating, for example sinusoidal, rotary motions applied to it, with which the elastic component of a real medium—such as, for example, a real liquid—can also be ascertained.

The factors determining highest measuring accuracy in the rheometer are, besides the exact determination of the torque and the stability of the ambient conditions, the lowest possible frictional mounting of the drive shaft and/or measuring shaft and, in particular, also the rigidity of the stand. In order to measure the respective torque acting instantaneously with minimal frictional forces and tensile forces, magnetic mountings and air mountings, for example, are known for the rotated components.

In FIG. 1 a known air bearing 5 is represented schematically. The radial bearing that is shown includes substantially a stator 51 which is fixed with respect to the stand or housing and a rotor disc or bearing disc 52 which is rotatably supported in the stator and which is firmly connected to the measuring shaft 3. The bearing disc 52 serves for accommodating axial loads acting on the measuring shaft 3, for example weight of the measuring shaft 3 and measuring elements, and is supported in relation to the stator 51 by air flowing through. The supply devices as well as feed lines and discharge lines for the air are not represented in FIG. 1.

In the evaluating unit 13 the measured values obtained are linked, in a manner known as such, with the temperature of the sample, with the height of the measuring gap 1 and also with the constants of the instrument, and the rheological data of the medium sample 19 can be computed therefrom.

In this connection an actual instantaneous height S of the measuring gap 1 also has a great influence on the measuring accuracy. The height S is adjusted or set by a positioning unit, for example a screw spindle 10 or a differently configured precise mechanical linear feed, by lowering the lower measuring element 1b and/or by raising the upper measuring element 1a. The measuring elements 1a, 1b are carried by positioning elements 22, 70 actuated or carried by the positioning unit.

In FIG. 1 a conventional type of adjustment of the gap height S is represented. A torque motor 9 mounted on a stand 7 displaces the measuring element 1a carried by the upper positioning element 22 relatively with regard to the lower positioning element constituted by a base plate 70 by the positioning unit constituted by the screw spindle 10. For gap-height setting, regulation of the feed motor 9 is effected by the values measured by a spacing-measuring or length-measuring unit 8, operating in non-contacting manner, arranged on the spindle 10. Length-measuring units known as such, such as, for example, potentiometers, incremental displacement transducers, inductive transducers or dial gauges, in each case measure the distance between the positioning elements 22, 70 and/or between the spindle nut 10a and a fixed point on the stand 7 or on the base plate 70 or other fixed points. Measurement of the actual spacing X can be effected both absolutely, by appropriate adjustment for the measuring geometry used in the given case on the elevating, feed and adjusting system or on the positioning unit, and relatively, i.e. starting from the zero point of the gap ascertained in each case by suitable processes, for example by the rise in torque when the measuring elements 1a and 1b touch one another.

The use of stepper motors, in order to carry out a controlled positioning of the positioning elements relative to one another without a need to carry out a spacing measurement, is also known. In this case, for example, the position of the upper measuring element 1a is ascertained, proceeding from a starting position or initial position of the spindle 10, by counting the rotational steps in, or contrary to, the clockwise direction and by multiplication of the steps by the step angle for defined feed.

Hence under constant ambient conditions predetermined gap heights S can be started up with micrometer precision, and at the same time the necessary feed within the mm range or cm range for introducing the sample medium 19 into the measuring gap 1 or for exchanging the measuring elements 1a, 1b can be achieved.

U.S. Pat. No. 6,499,336 and its counterpart Austrian Patent AT 409 304 B, show, furthermore, the possibility of determining the height of the measuring gap 1 as exactly as possible by displacement sensors operating in a non-contacting manner, for example by inductive or at least magnetic displacement sensors, and for keeping the gap height S constant by regulation of the adjustment of the spindle nut 10a on the stand 7. In this case the actual spacing between the two measuring elements 1a, 1b is determined by sensors operating in non-contacting manner which are arranged on the measuring elements. Setting or regulation of the spacing between the two measuring elements 1a, 1b by the positioning motor 9 for the stand spindle 10 is effected by the evaluating unit 13, specifically on the basis of the measured values of this spacing measurement.

Viscoelastic substances display a mixture of viscous and elastic behavior under shear. In the shear test, normal forces $N_F$ arise in the axial direction of the measuring shaft or measuring axle 3, which constitute a measure of the elastic component in the flow behavior. Under shear, normal forces of up to a few 10 N may arise; the pressure that is acting on the two measuring elements 1a, 1b in the axial direction is measured with different sensor arrangements known as such.

Whereas U.S. Pat. No. 6,167,752 B determines the normal forces on the air-supported measuring shaft via spacing sensors, U.S. Pat. No. 6,892,583 B proposes, for example, the measurement of the normal forces by use of piezosensors in the rheometer measuring plate itself. Further possibilities for the determination are also known.

The values of the normal force $N_F$ measured in highly diverse ways are, in particular, analogously available without restriction, as are also all previously described possibilities and known variants, for the procedure and form of the gap-height correction according to the invention described in the following.

In FIG. 1 the variant of the measurement of the normal force $N_F$ presented in U.S. Pat. No. 6,167,752 A by a sensor 6 on the air bearing 5 of the measuring shaft 3 is represented. In this case the axial adjustment or deflection of the upper measuring element 1a and hence of the measuring shaft 3 brought about by the forces acting in the axial direction is determined by spacing sensors or displacement sensors 6 operating in non-contacting manner and is translated into normal force $N_F$.

Normal forces exert pressure on the measuring elements 1a, 1b axially relative to the measuring shaft and bring about, as a rule, an axial opening or widening of the gap 1. In this connection, in addition to the deficient rigidity and/or a torsional flexing of the stand 7 further influences, partly depending on the structural design of the rotary rheometer 100, also play a role, for example the rigidity of the measuring-shaft mounting 5, a possible clearance of the spindle nut 10a on the height-adjusting spindle or feed spindle 10 and such like.

The viscosity values that are obtained consequently contain an error which is inherent in the instrument, the magnitude of which varies with the level of the normal force $N_F$.

The method described in Austrian Patent AT 409 304 B for measurement and correction of the spacing or change of spacing of the measuring elements ascertained by the displacement sensor 6 constitutes a proven measure for correcting the gap height S, for example in tests for determining the temperature dependence of the rheological properties. In these and similar long-term tests, the normal forces $N_F$ change on a similar time scale as the temperature drift, and hence the gap height S can be regulated via the sluggish mechanical system or via the positioning unit. The regulation by mechanical systems shows certain sluggishness in its response. By reason of the mechanically functioning feeds or positioning units, in practice it is not readily possible to advance into the sub-micrometer range.

The proposed compensation of the gap height also fails in the case of rapidly changing test conditions or in the case of measurement within the short-term range, such as, for example, in the case of shear-jump tests which examine the behavior of thixotropic or rheopectic substances upon a sudden change in the shear loading.

Thixotropic behavior results in a decrease in the original structural strength and hence a lowering of the viscosity during a shear-loading phase and more or less complete reconstruction during a following rest phase. This reduction and the build-up following it are reversible processes. Almost all dispersions, suspensions, emulsions, foams—such as, in particular, pastes, creams, ketchup, paints and such like—display thixotropic behavior, whereas rheopectic substances arise rather seldom in practice and display an increase in structural strength under shear loading. For the purpose of examining these properties, typically shear-jump tests are carried out with a rotary rheometer.

Other features which are considered as characteristic for the invention are set forth in the appended claims.

Although the invention is illustrated and described herein as embodied in a process and a rheometer for determining the rheological properties of materials, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
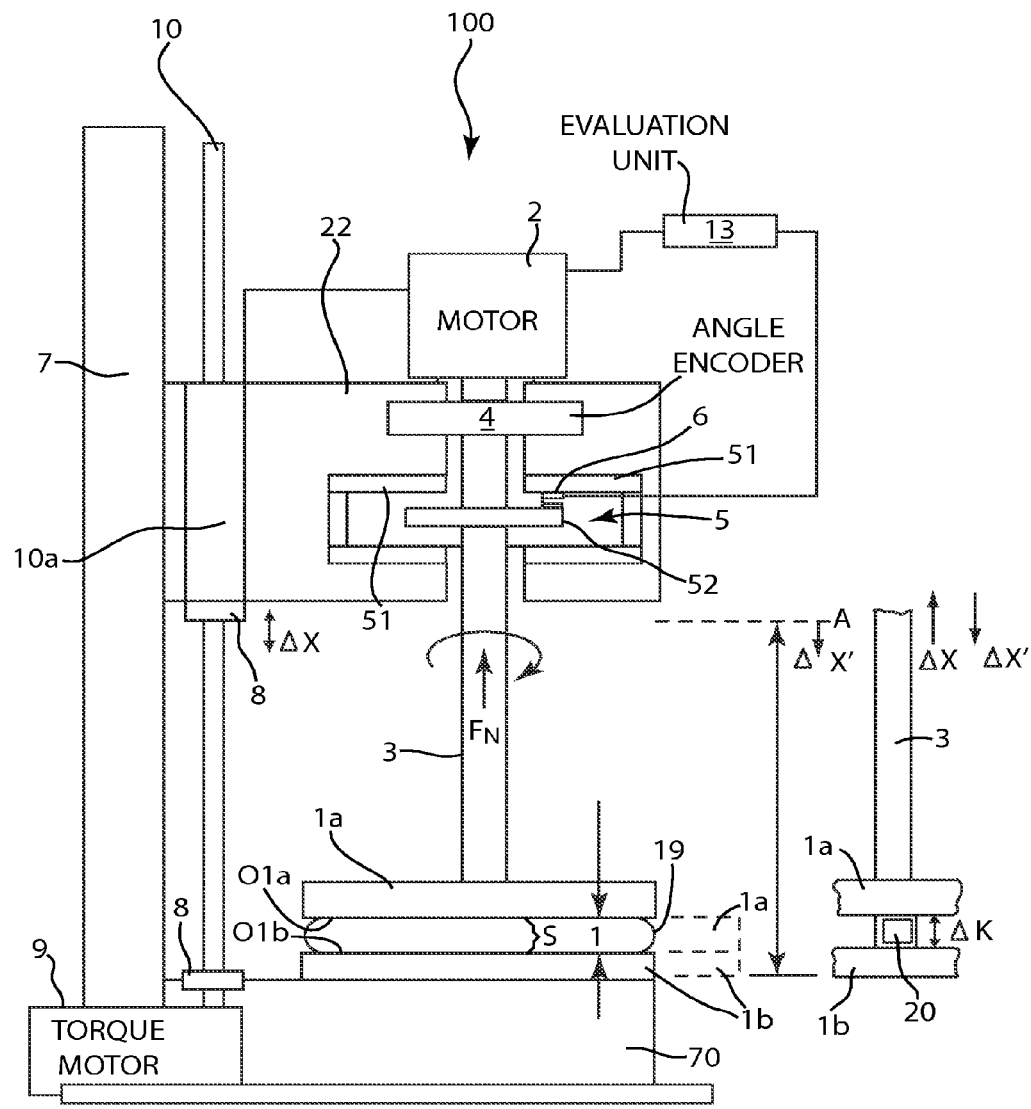
FIG. 1 is an illustration showing a prior art structure of a rotary rheometer.
Figure 2A:
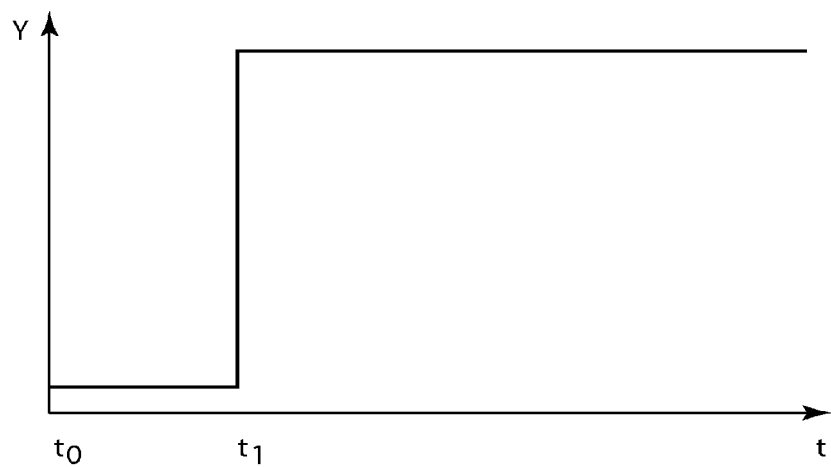
FIG. 2A is a graph showing schematically a jump function of viscosity upon an occurrence of a shear loading at time starting from this time, normal forces $N_F$ build up.
Figure 2B:
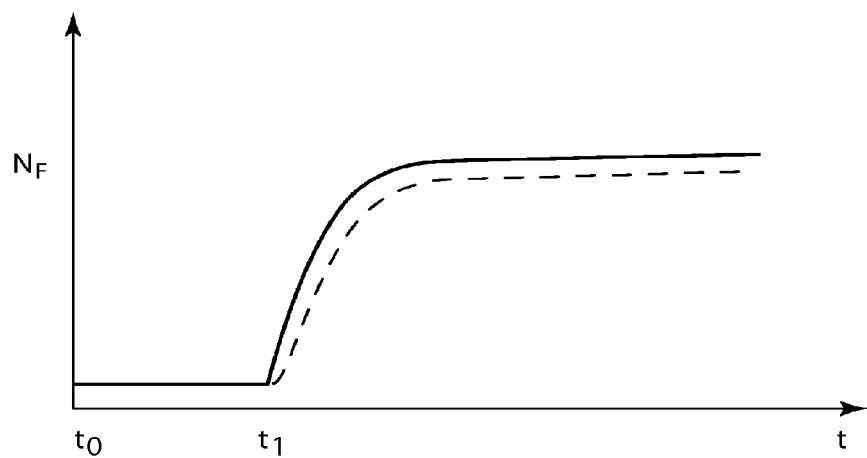
FIG. 2B is a graph showing with a continuous line the normal forces arising in the case of resetting of a gap height S taking place immediately in accordance with the procedure according to the invention. Here the influence is shown of the rack parameters and positioning-element parameters with respect to rigidity etc. on the normal forces which in themselves are in turn to characterize the sample substance. The dashed line represented in FIG. 2B indicates the measured normal forces to the extent that re-regulation of the gap height S is effected slowly or does not occur.

In order to compensate the change in the height of the measuring gap, the influences and the differing contributions of the rack, of the measuring shaft, of the positioning unit, i.e. of all the parts of the rotary rheometer situated between the measuring elements or carrying and actuating the latter, have to be taken into account, or the effect thereof has to be compensated in total by suitable measures for keeping the gap height constant—that is to say, in concrete terms, by appropriately chosen feed device or adjusting device.

In this connection, quite generally the following relationship holds for the gap height S to be corrected:

$$\Delta S_{corr} = f(N_F).$$

Depending on the type of construction, in this way differing parasitic influences in cooperation with the normal force acting or arising are able to change the actual height of the measuring gap.

The overall widening of the measuring gap by reason of normal forces is determined by the sum of the contributions s of deficient rigidity of the bearings, spindle-nut clearance, deficient rigidity of the stand, etc.

In this connection, for the change $\Delta S_{corr}$ in the width or height of the gap the following holds:

$$\Delta S_{corr} = \Sigma(s_{spindle\ nut} + s_{axial\ bearing} + s_{clearance\ and\ rigidity\ of\ the\ positioning\ elements} + s_{support\ of\ the\ measuring\ elements} + s_{air\ bearing} + s_{stand\ buckling} + s_{magnetic\ bearing} \ldots) = f(N_F)$$

In this connection the individual contributions are not available for the purpose of correction either metrologically as a single contribution or computationally.

However, the overall influence can be determined for the respective rheometer, specifically independently of the details arising from the chosen measuring geometry, and is taken into account in the calibrating function.

In order to exclude these influences, a process for determining the rheological properties of medium samples of the type initially specified is characterized.

In order to compensate the influence of errors by virtue of widening of the measuring gap as a consequence of normal forces acting or arising in the course of the measurement, this widening of the gap, which is a specific variable for a concrete instrument in the given case by reason of its instrument parameters, for example rack rigidity, bearing clearance of the drives, flexural rigidity etc., is measured in a calibrating step as a function of the normal force. Subsequently the calibration table or calibration curve obtained in this way is used for the purpose of controlling electrical actuators which compensate the gap height as a function of the normal forces actually arising in the measuring procedure practically without temporal delay. The result of the normal-force measurement which is performed is used for the purpose of creating a control signal and is translated in the evaluating and control unit into a control voltage for the actuators. Hence the widening of the gap as a consequence of the deficient rigidity of the stand, or of a removal of the positioning elements or of the measuring elements carried by them from one another by the normal forces, is compensated in total.

In accordance with the invention, for the purpose of compensating the change in gap height it is proposed to register the instrument parameters metrologically in a first step and to store them as part of the calibrating function in the evaluating unit 13.

To this end, in the absence of a medium sample the actual measuring gap 1 is controlled to height zero by the mechanical spindle feed or the positioning unit, so that the two measuring elements 1a, 1b just touch one another or bear against one another and $N_F=0$. Now, by the positioning unit or by actuation of the spindle via the positioning elements 22, 70 the measuring plates 1a, 1b are pressed against one another with precisely defined, differing individual loading steps, which in particular are increased in each instance, whereby the normal forces $N_F$ resulting for the individual steps are measured or determined. At the same time, the positioning displacement required for this or travelled by the positioning unit or by the spindle is ascertained.

Then pairs of measured values relating to the respective positioning displacement, which is equated to the widening of the rack for the normal force $N_F$ arising in the given case, are created in the form of a calibration table. Hence a function $$\Delta S_{corr} = f(N_F) \text{ is available for measurements to be performed.}$$

In the course of the test procedure with real medium samples 19, the calibrating function obtained in this way is used for the control of sliding actuators 11, 11a to 11d, 12, 12c (see, FIGS. 3-7) provided for the adjustment of the gap height of at least one of the measuring plates 1a, 1b. In this connection, by reason of the respectively instantaneous measured value of the normal force $N_F$ the evaluating and control unit 1330 (see FIG. 3) emits a control signal ascertained from the calibration data to a voltage generator 30 for the sliding actuators, for example piezoactuators, which therefore immediately execute a linear feed of at least one of the measuring elements 1a, 1b towards the respective other measuring element 1b, 1a—that is to say, in the opposite direction to the gap widening or gap-height enlargement. This linear feed corresponds to the ascertained positioning displacement of the positioning unit or of the spindle, which in the calibration process has generated a normal force that corresponds to the normal force arising instantaneously in the test. Hence in measuring operation the widening of the gap caused by normal forces arising can be compensated in almost delay-free manner, i.e. the widening of the gap brought about by reason of deficient rigidity of the rack by reason of the normal forces is compensated. During the measurement the widening of the gap expansion to be expected by reason of the normal forces $N_F$ arising is corrected by immediate very fine adjustment of the height of the measuring gap by the sliding actuators.

Advantageously, at least one solid-state actuator is employed which readjusts the spacing of the measuring plates 1a, 1b from one another—that is to say, the gap height S—towards the originally set value and therefore keeps it constant.

Such solid-state actuators may be piezoactuators (PZT), electrodynamic drives or even electrostrictive actuators (PMN). Essential in this regard is the direct, rapid conversion of the electrical voltage signals into a linear motion with correspondingly fine resolution.

The advantage of these sliding actuators lies—in the case of an, in itself, relatively small overall adjusting displacement—in their small increments and their extremely short response-times in comparison with mechanical arrangements. Whereas piezoactuators are distinguished by high temperature stability, electrostrictive actuators display slighter hysteresis behavior. Both display a defined relationship between applied control voltage and deflection.

In accordance with the invention it is proposed to arrange sliding actuators of such a type at respectively suitable positions in the rotary rheometer 100 in such a way that the changes of height in the gap 1, caused by the normal force $N_F$ and rigidity of the stand, between the measuring elements 1a, 1b can be compensated as quickly as possible.

For the control voltage $U_{piezo}$ the following holds:

$$U_{piezo}=f(\Delta S_{corr})=f'(N_F).$$

For the purpose of obtaining the adjusting displacement a linear feed actuator or a number of linear feed actuators may be provided.

In particular when a regulation to constant gap height S does not take place, by reason of the normal-force value currently measured the sliding actuators can immediately have applied to them the voltage values determined in advance by use of the calibration table or calibration curve, and the linear feed of the sliding actuators and hence the adjustment of the gap height which is immediate or which takes place without delay can be controlled. In this way, the inevitable delay by virtue of a control loop is dispensed with. In this way a measurement of the normal force $N_F$—taking place, for example, with a spacing-measuring sensor 6 on the rotor disc 52—can be translated into changes in gap height assigned by the calibrating function, and the mechanical setting of the gap height with the actuators is effected with the assigned voltage signals.

FIGS. 3 to 7 show advantageous embodiments of rheometers with differing positioning of actuators for compensating a widening of the gap by virtue of normal forces arising.

FIG. 1, representative of FIGS. 3 to 7, shows schematically the fundamental or basic structure of the rotary rheometer 100 according to the invention with the measuring motor 2 and with the measuring shaft 3 which carries the upper measuring element 1a which here takes the form of a measuring plate.

The medium sample 19 is introduced between the lower measuring element 1b, taking the form of a fixed measuring plate, and the upper measuring element 1a, likewise taking the form of a measuring plate. The upper measuring plate is, as a rule, constructed to be smaller than or the same size as the lower measuring plate 1b. Commercial rheometers possess easily interchangeable measuring elements 1a and 1b with plate surfaces 01a and 01b by virtue of a quick-closing lock together with non-contacting measuring-element recognition.

The measuring elements 1a, 1b, here taking the form of measuring plates, can be adjusted directly via the linear feed of the positioning unit 10 taking the form of a screw spindle with spindle nut 10a, after calibration to the geometry being used, or indirectly, after prior determination of the zero point relative to said feed, in order to set the measuring gap. Where appropriate, the evaluating accuracy can be increased by means of a non-contacting measuring system according to Austrian Patent AT 409 304 B for determining the actual spacing.

On the basis of FIG. 1 it will furthermore be explained how the calibration function is ascertained and how the latter finds application in measuring operation. For the ascertainment of the calibration function—as represented by dashed lines—with measuring elements 1a, 1b applied directly against one another, i.e. without sample 19, the spacing X resulting in this position between a positioning element 22 carrying the upper measuring element 1a and the rack 7 supporting the lower measuring element 1b, which spacing is measured with the spacing-measuring device 8, is gradually reduced. By rotation of the spindle 10, the positioning element 22 is lowered in the direction towards the positioning element 70 constituted by a base of the rack 7 in an appropriate number of loading steps by a predetermined value $\Delta X$ in each case. Measurement of this feed value may be undertaken in arbitrary manner. Spacing-measuring devices 8 of such a type are known from the state of the art, as is the positioning by stepper motors. The normal-force values resulting in this case between the measuring elements 1a, 1b are recorded herewith the measuring unit 6. Highly diverse arrangements for determining the normal forces arising are known from the state of the art and may be employed for the process according to the invention. The measured normal-force values with the assigned feed displacements constitute the calibrating function. In measuring operation, upon occurrence of normal forces a diminution of the measuring gap S is effected with the aid of the stored calibrating function by the actuators which are provided, by the positioning elements 22 and 70 being approximated to one another in the axial direction relative to the measuring shaft 3 by the value $\Delta X'$, the values $\Delta X'$ having been determined by the measured normal-force values $N_F$ arising in each case, and corresponding to the initially ascertained values $\Delta X$.

Recording units or measuring units of such a type are generally designated by reference symbol 6, without restrictions arising in this connection with regard to the position or with regard to the place of attachment. The type and the structure of recording units or measuring units 6 of such a type can also be chosen arbitrarily. For example, optical or inductive measuring units 6, or even measuring units 6 operating in accordance with other measuring principles, could also be employed. The arrangement and design according to the invention of the recording or measuring unit 6 result in a preferred embodiment, because it can be created easily and it measures exactly.

The values $\Delta X$ and $\Delta X'$ are to be set a priori to be of equal magnitude. Under certain circumstances another correction factor or a weighting could be undertaken for the purpose of taking temperature influences or other parameters into account.

In FIG. 1 on the right there is a representation of how the measuring elements 1a, 1b are pushed apart with a normal force ΔK for the purpose of ascertaining the calibrating function with the aid of a force-application unit 20. A pressure-application unit 20 of such a type may be, for example, a piezoactuator which given an appropriate application of voltage implements a change of dimension in the direction of the axis of the measuring shaft 3. In appropriate loading steps differing forces ΔK can be applied from the inside onto the measuring surfaces of the measuring elements 1a, 1b. The positioning unit which sets the spacing of the measuring elements 1a and 1b, in this case the measuring spindle 10, is then adjusted correspondingly until the normal forces AK ascertained with the measuring unit 6 have been nullified. In this position, by use of the spacing-measuring unit 8 the spacing is established with which the two positioning elements 22, 70 have been moved away from one another, and these measured spacing values are assigned to the normal forces AK exerted in the individual loading steps, by which the calibrating function is created.

Application of the value ΔX' with the actuators always has to be effected in such a manner that a diminution of the measuring gap 1 results.

Figure 3:
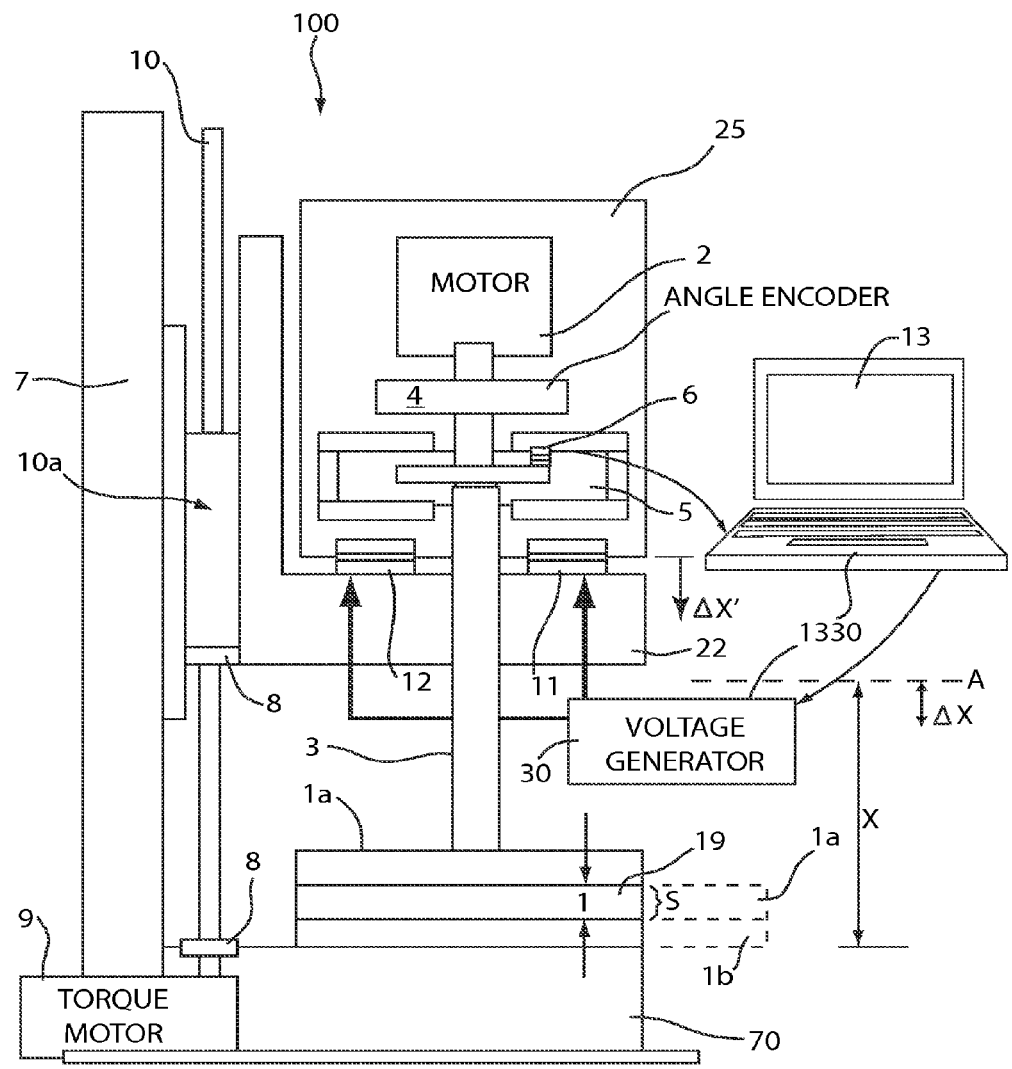
FIGS. 3 to 7 are illustrations showing embodiments of rheometers according to the invention.

FIG. 3 shows schematically the incorporation of actuators 11, 12 for gap-height correction on the lifting device of the stand 7 or on the screw spindle 10. The piezoactuators 11, 12 may have been fitted directly to the mounting of the measuring motor and/or to the rack 7 or to the feed mechanism or height-adjusting mechanism thereof and/or to the positioning elements and/or to the base plate and are controlled by the voltage generator 30 of the evaluating and control unit 1330. In the present case, the positioning element 22 carries a bearing block 25 which contains the measuring motor 2, inclusive of measuring shaft 3 and upper measuring element 1a, as well as the angle encoder 4, the air bearing 5 and a normal-force measuring device or a displacement sensor 6 suitable for this purpose. The bearing block 25 can be displaced, i.e. lowered, with the piezoactuators 11 and 12 in linear manner contrary to the action of the normal force $N_F$. Control of the actuators 11, 12 is undertaken via the voltage generator 30 by the evaluating unit 13—that is to say, by the unit 1330 containing the calibrating function in stored form.

Designated by X in FIG. 3 is the spacing between the upper positioning element 22 and the lower positioning element 70, if they are located in a position in which the measuring elements 1a, 1b bear against one another, i.e. that the upper measuring element 1a would have to be lowered by the represented gap height S to the initial height A in order to perform the initial calibration. In the course of the ascertainment of the calibration function, the two positioning elements 22, 70 are approximated to one another from the position that is represented until the measuring elements 1a, 1b touch one another and the spacing X obtains. Upon further rotation of the screw spindle 10, under appropriate application of pressure to the two measuring elements 1a, 1b no further approximating of these two measuring elements 1a, 1b takes place, but, by reason of the non-rigidity of the rack or of all the parts of the rheometer loading the measuring elements 1a, 1b, the screw nut 10a can be approximated further to the positioning element 70 upon rotation of the spindle 10, although the upper measuring element 1a cannot change its position. The displacement ΔX travelled is established with the measuring unit 8. The calibrating function consequently results by virtue of the linking of the displacement units ΔX established for differing loadings with the normal forces arising between the measuring elements 1a and 1b, which are measured by the measuring unit 6, for example in the bearing of the measuring shaft 3. In order to be able to employ the calibrating function in measuring operation, upon detection of a normal force $N_F$ arising, which attempts to push the upper measuring element 1a upwards, an appropriate counterforce is exerted, by the upper positioning element 1a being pushed downwards. In the present case, however, the positioning element 22 is not adjusted downwards, but rather a force directed downwards in the direction towards the lower measuring element 1b is exerted on the bearing block 25 of the measuring shaft 3, by the bearing block 25 being adjusted by the displacement ΔX' with the aid of the actuators 11, 12 in the direction towards measuring element 1b. As already stated previously, the adjusting displacement ΔX' corresponds to the adjustment value ΔX which was ascertained with the measuring unit 8.

The actuators may, for example, also have been provided or may act below the lower measuring plate 1b, on the mounting of the spindle 10; it is essential that a diminution of the height S of the measuring gap 1 is obtained by their actuation.

Figure 4:
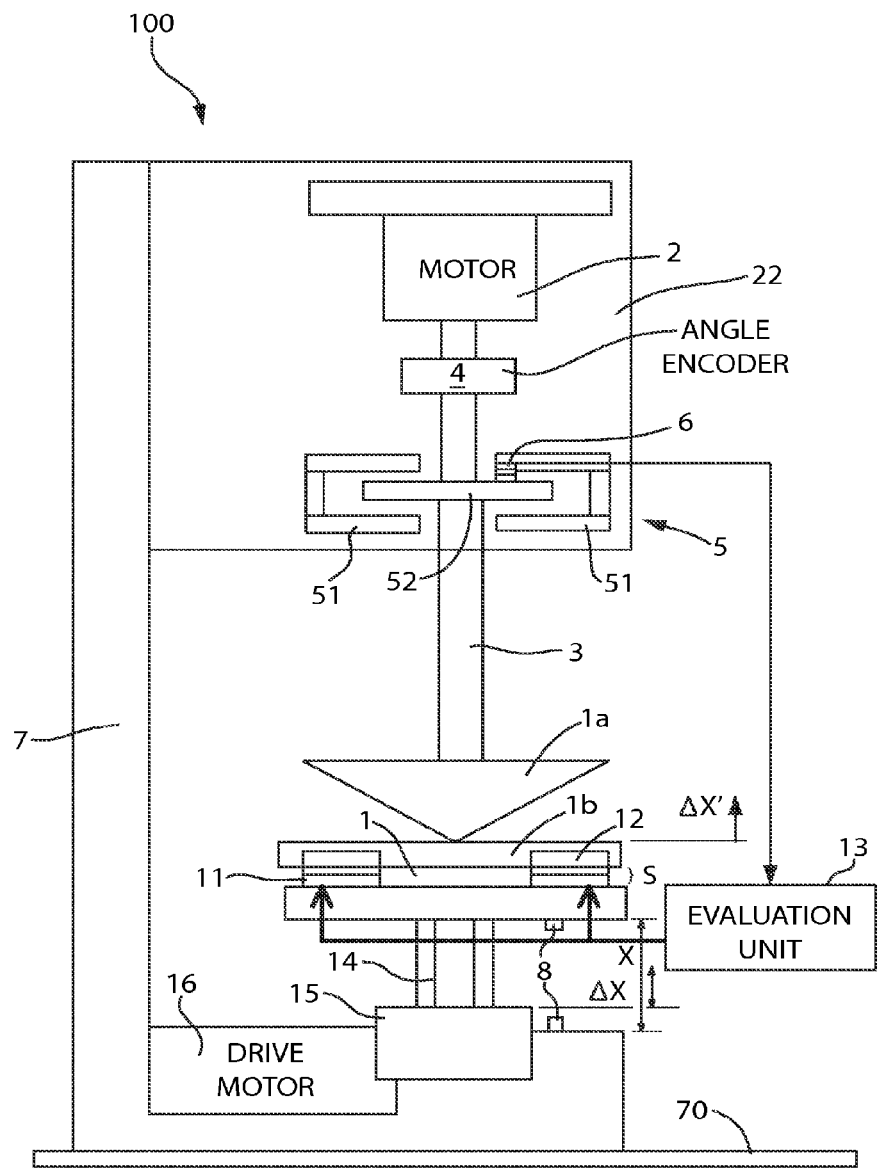

FIG. 4 shows an alternative embodiment. The positioning element 22 takes the form of a bearing block and includes the measuring motor 2, the angle encoder 4 and the bearing 5 and is firmly connected to the rack 7. The upper measuring element 1a is constructed here as a measuring cone; the lower measuring element 1b as a measuring plate. The lower measuring element 1b rests on a lifting table 14 which is displaceably supported axially relative to the measuring shaft 3 in the rack 7 and is equipped with an arbitrary linear drive, for example consisting of spindle 10, thrust bearing 15 and drive motor 16.

In FIG. 4, in the course of the calibration with the aid of the thrust bearing 15 the differing normal forces are applied during the series of loading steps, and the relative change ΔX arising in the process in the spacing X between thrust bearing 15 and the lower measuring element 1b is ascertained. In the course of the measuring process, with the aid of the calibrating function with the actuators 11 and 12 the normal force established with the measuring unit 6 is then opposed, and the adjusting displacement ΔX' is imposed on the lower measuring plate 1b. This adjusting displacement ΔX' corresponds substantially to the adjusting displacement ΔX which was ascertained by the measuring units 8 in the course of calibrating.

The actuators 11, 12 arranged on the lifting table 14 displace the lower measuring element 1b directly relative to its set bearing position in the direction towards the upper measuring element 1a.

It is also possible here, in addition, to provide the arrangement, described above, of the actuators on the upper part of the measuring-motor bearing 5 or on the lower bearing 15.

Figure 5:
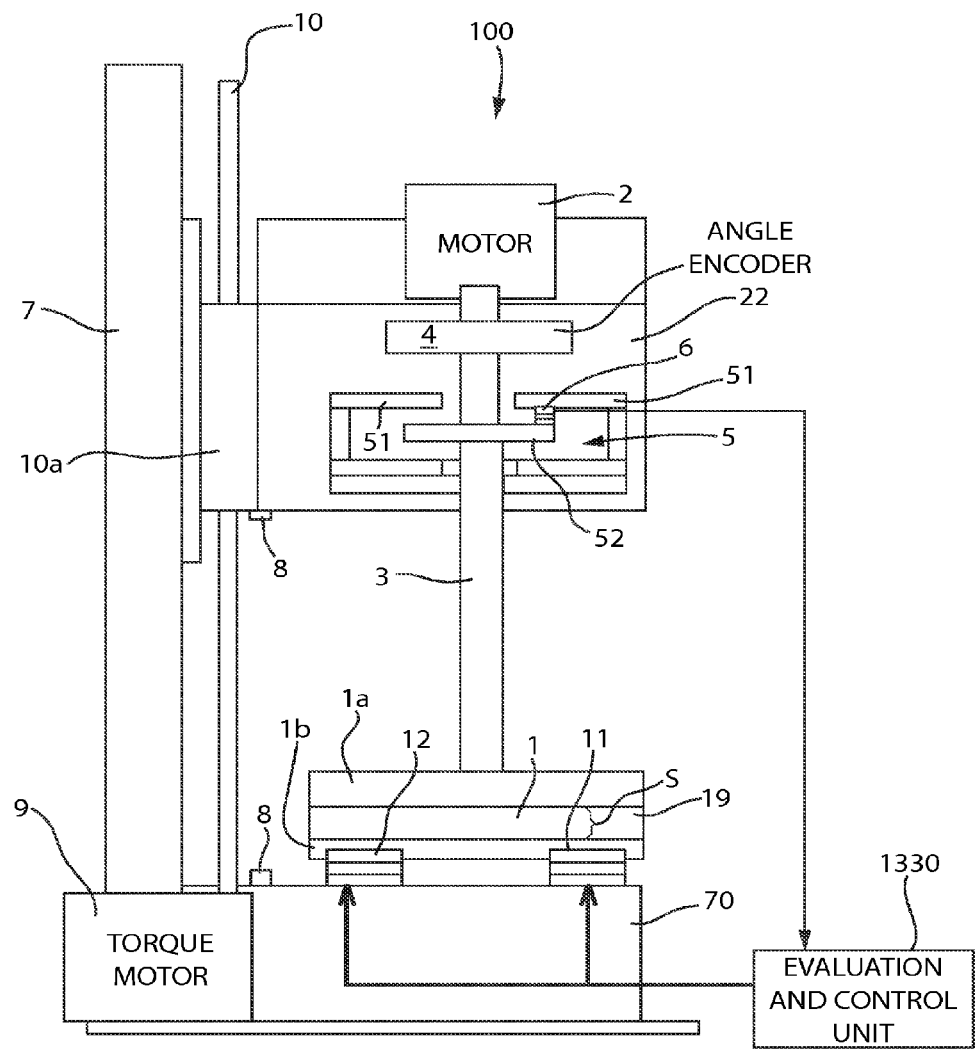

FIG. 5 shows schematically a further configuration, according to the invention, of a rheometer 100. The piezoactuators 11, 12 are fitted here between the firm base 70, acting as positioning element, of the stand 7 and the lower measuring element 1b.

Ascertainment of the calibration function in the case of the rheometer represented in FIG. 5 is effected in a manner comparable to that for the rheometer according to FIG. 1. Application of the adjusting displacement ΔX' for the purpose of compensating the normal forces is effected by raising the lower measuring element 1b by the actuators 11, 12.

In principle, use may be made of arbitrary linear drives, such as linear motors, pneumatically driven adjusting devices, Uhing drive nuts and such like.

At this point it will be noted that, quite generally, the adjusting elements 22 and 70 which are adjustable relative to one another in the rack 7 may be configured in such a manner that both positioning elements are movable relative to one another or one of the two positioning elements is movable relative to the respective other positioning element, which other positioning element may be arranged in a fixed position on the rack 7, such as, for example, a base plate of the rack 7.

Figure 6:
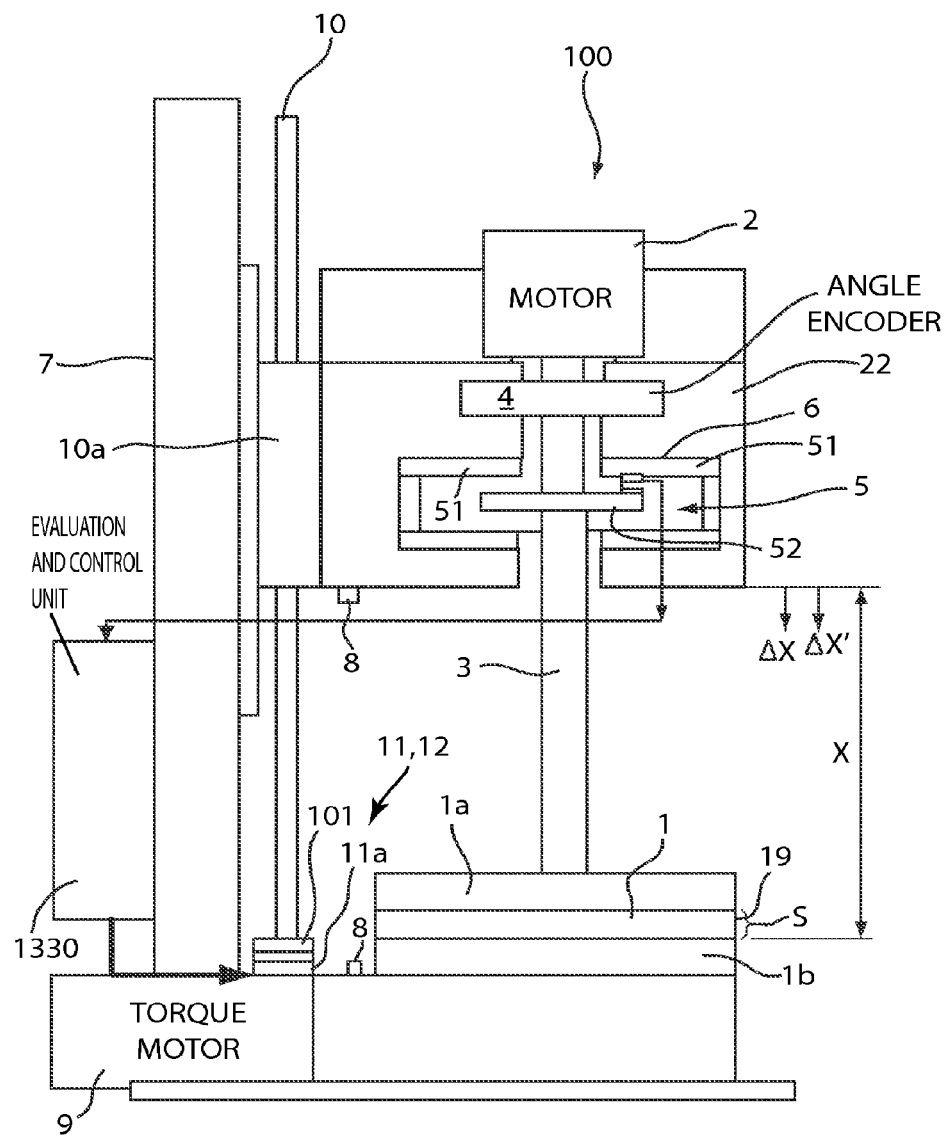
Figure 7:
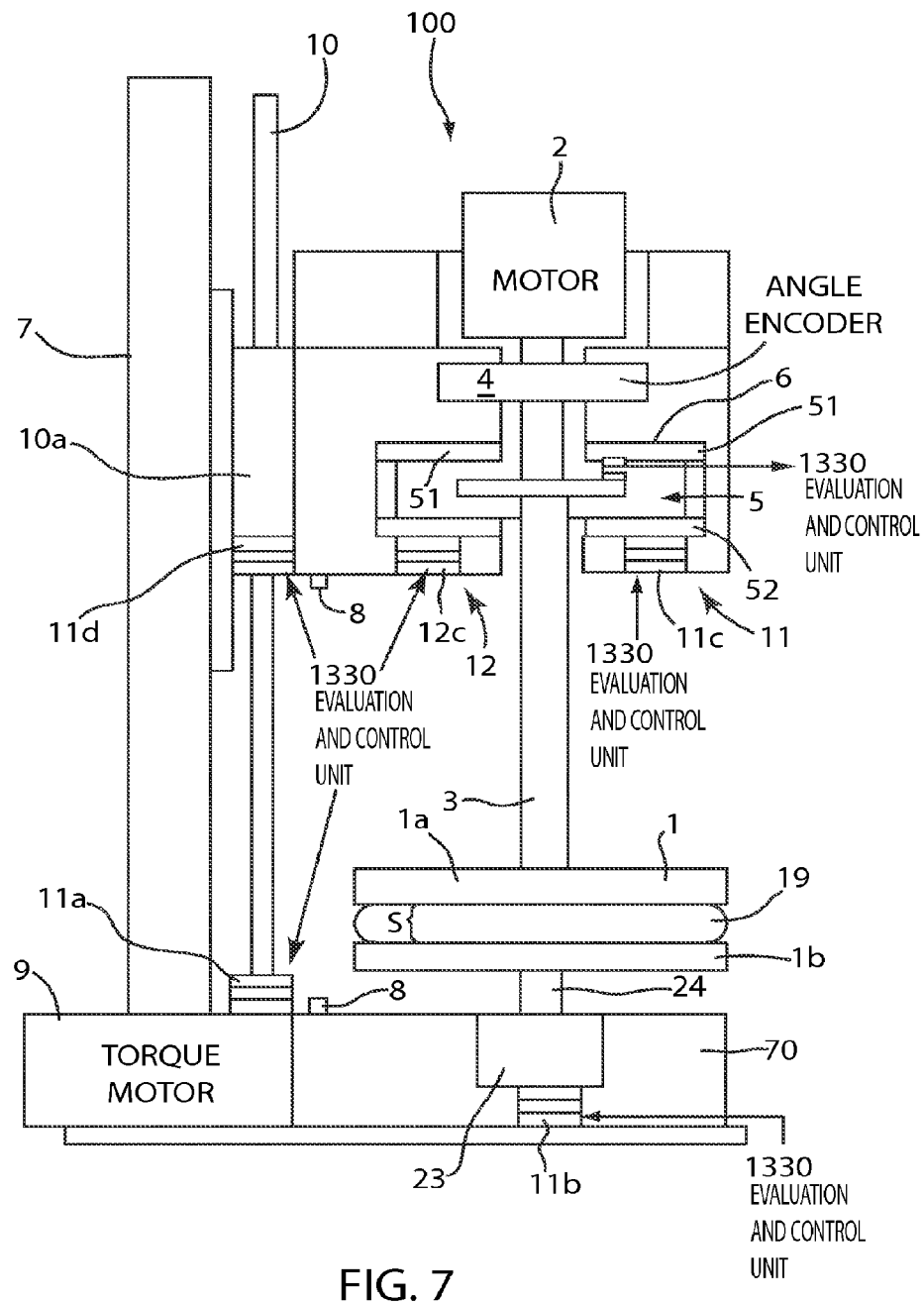

From the exemplary embodiments shown in FIGS. 6 and 7 it is evident that the correction, to be implemented in accordance with the invention, of the normal-force influence on the gap height S is possible by piezoactuators, 11a to 11d and 12c in differing embodiment variants of a rotary rheometer 100 according to the state of the art at differing positions of the rheometer 100.

FIG. 6 shows the actuator 11a for the purpose of compensation at the foot 101 of the spindle 10 or on the spindle mounting arranged there.

FIG. 7 shows various variants of the fitting of actuators 11a to 11d, 12c to a rheometer 100 with measuring motor 2. Here the shearing force is applied to the medium sample 19 between the measuring elements 1a, 1b by rotation of the lower measuring element 1b with a motor 23 with shaft 24. The motor 23 and/or the motor 2 measure(s) the resulting moment. An actuator 11a may have been provided on the mounting of the spindle 10; the fitting of at least one actuator to the motor mounting of the lower measuring element 1b and/or the fitting of actuators 11c, 12c to the mounting 5 of the rotating bearing disc 52 and/or of the measuring motor 2 and/or the fitting of actuators 11a, 11d to the measuring spindle 10 is/are possible.

In accordance with the respective arrangement of the actuators on the individual structural elements of the rheometer, i.e. on the positioning elements and/or on the bearing block and/or on the spindle etc., the direction of force of the positioning forces exerted by the respective actuators has to be established, in order to counteract precisely the normal forces that arise in the measuring gap in the course of the measuring process.

The schematic actuators shown in all the figures may vary, depending on position, number and type.

Rheometers 100 pertaining to the state of the art with various driving and measuring variants, in particular those as described in the introduction, can be combined or retrofitted with the features of the rheometer according to the invention without difficulty.

Ascertainment of the calibrating function is effected with actuators shut down, i.e. the actuators employed or the mounting thereof can also contribute to the deficient rigidity of the overall system.

The invention claimed is:

1. A process for determining rheological properties of medium samples disposed in a measuring gap formed by measuring surfaces facing towards one another of two measuring elements of a rotary rheometer being rotated relative to one another, which comprises the steps of:
   measuring normal forces arising in the measuring gap perpendicular to the measuring surfaces with a recording unit and evaluating the normal forces via an evaluating and control unit;
   adjusting a height of the measuring gap with a positioning unit and with positioning elements actuated by the positioning unit, the positioning unit adjusting the positioning elements carrying the measuring elements relative to one another; and
   during the measuring process a value that has been set in a given case of a predetermined initial height of the measuring gap is kept constant in a substantially delay-free manner, by values of the normal forces arising being linked with values of a calibrating function ascertained previously in each case, and made available by a memory unit, the calibrating function describing a functional dependence between one of a change and enlargement of the height of the measuring gap and a normal force acting in the process in each instance on the measuring elements and, upon detection of the normal forces arising, the values derived from the calibrating function are drawn upon as control signals, with which at least one sliding actuator acting one of directly and indirectly on at least one of the two measuring elements substantially in delay-free manner or applying force to the measuring elements is driven, which by one of position adjustment and height adjustment of the respective measuring element performs an immediate resetting of the height of the measuring gap, changed by the normal forces exerted by the medium sample to be examined, to an originally set initial spacing.

2. The process according to claim 1, which further comprises:
   ascertaining the calibrating function $\Delta S = f(N_F)$ by the measuring elements being brought into reciprocal abutment in a first step while avoiding a generation of a normal force; and
   performing one of:
      in that in several loading steps exactly defined in their magnitude at least one of the measuring elements is then pressed against the respective other measuring element by the positioning unit via the positioning elements and for the respective loading the associated or requisite value of an adjusting displacement one of produced and travelled by one of the positioning unit and the positioning elements for exerting the loading is ascertained; and
      in that in several loading steps exactly defined in their magnitude a predetermined force, enlarging the height of the gap, is then exerted from inside the measuring gap on the measuring elements in each instance and the adjusting displacement of one of the positioning elements and the positioning unit is measured which is required in order to compensate or nullify the force exerted by the respective loading by widening of the gap.

3. The process according to claim 1, wherein upon an occurrence of the normal force bringing about an enlargement of the height of the gap in a measuring operation the change in the gap is compensated by a voltage signal corresponding to the normal force and predetermined by or derived from the calibrating function and which was assigned to the normal force in the course of a calibrating process, by an adjustment of at least one measuring element being effected with the actuator for one of changing and diminishing the gap height contrary to a direction of the normal force that has arisen.

4. The process according to claim 1, which further comprises displacing the measuring element via the actuator perpendicularly to a plane of at least one of the measuring surfaces.

* * * * *